United States Patent
Okumura

(10) Patent No.: US 10,446,702 B2
(45) Date of Patent: Oct. 15, 2019

(54) PHOTOELECTRIC CONVERSION MATERIAL AND SOLAR CELL USING THE SAME

(71) Applicant: Panasonic Intellectual Property Management Co., Ltd., Osaka (JP)

(72) Inventor: Hiroko Okumura, Osaka (JP)

(73) Assignee: Panasonic Intellectual Property Management Co., Ltd., Osaka (JP)

(*) Notice: Subject to any disclaimer, the term of this patent is extended or adjusted under 35 U.S.C. 154(b) by 105 days.

(21) Appl. No.: 15/887,995

(22) Filed: Feb. 3, 2018

(65) Prior Publication Data

US 2018/0233608 A1    Aug. 16, 2018

(30) Foreign Application Priority Data

Feb. 15, 2017  (JP) .................. 2017-025726

(51) Int. Cl.
  *H01L 31/032*   (2006.01)
  *C07F 7/30*     (2006.01)
  *H01L 31/036*   (2006.01)

(52) U.S. Cl.
  CPC ........... *H01L 31/032* (2013.01); *C07F 7/30* (2013.01); *H01L 31/036* (2013.01); *Y02E 10/50* (2013.01)

(58) Field of Classification Search
  CPC . H01L 31/032; H01L 31/036; H01L 31/0735; H01L 31/0745; C07F 7/30
  USPC .................................. 136/242–265
  See application file for complete search history.

(56) References Cited

U.S. PATENT DOCUMENTS

| | | | |
|---|---|---|---|
| 2003/0151117 A1 | 8/2003 | Vogg et al. | |
| 2014/0076388 A1* | 3/2014 | King | H01L 31/0725 136/255 |
| 2016/0190244 A1 | 6/2016 | Lee et al. | |

FOREIGN PATENT DOCUMENTS

| | | |
|---|---|---|
| EP | 2755241 | 7/2014 |
| JP | 61-228613 | 10/1986 |
| JP | 2003-528796 | 9/2003 |
| JP | 2016-127267 | 7/2016 |
| WO | 2013/035686 | 3/2013 |

OTHER PUBLICATIONS

Comedi, D., and I. Chambouleyron. "Dopant Impurity-Induced Defects in p-Type Doped Hydrogenated Amorphous Germanium." Applied Physics Letters, vol. 69, No. 12, 1996, pp. 1737-1739., doi:10.1063/1.118014. (Year: 1996).*

(Continued)

*Primary Examiner* — Eli S Mekhlin
*Assistant Examiner* — Kourtney R S Carlson
(74) *Attorney, Agent, or Firm* — Renner, Otto, Boisselle & Sklar, LLP

(57) ABSTRACT

A photoelectric conversion material includes a germanane derivative having a composition represented by $Ge_xM_yH_z$. M includes at least one of Ga and In. $X \geq Y$, $X \geq Z > 0$, and $X+Y=1$ are satisfied. A solar cell includes: a first electrode having electrical conductivity; a second electrode having electrical conductivity; and a light-absorbing layer between the first electrode and the second electrode, the light-absorbing layer converting incident light into electric charge. The light-absorbing layer includes the photoelectric conversion material above.

10 Claims, 16 Drawing Sheets

(56) References Cited

OTHER PUBLICATIONS

Comedi, D., et al. "Properties of Gallium-Doped Hydrogenated Amorphous Germanium." Physical Review B, vol. 52, No. 7, 1995, pp. 4974-4985., doi:10.1103/physrevb.52.4974. (Year: 1995).*

Fajardo, F., and I. Chambouleyron. "Structural and Optoelectronic Properties of Indium-Doped a-Ge:H Thin Films." Physical Review B, vol. 52, No. 7, 1995, pp. 4965-4973., doi:10.1103/physrevb.52.4965. (Year: 1995).*

Abstract of Fajardo, F., et al. "Indium and Gallium p-Type Doping of Hydrogenated Amorphous Germanium Thin Films." Applied Physics Letters, vol. 64, No. 24, 1994, pp. 3273-3275., doi:10.1063/1.111307. (Year: 1994).*

Elisabeth Bianco et al., "Stability and Exfoliation of Germanane: A Germanium Graphane Analogue", ACS Nano, vol. 7, No. 5, Mar. 19, 2013, pp. 4414-4421.

Maxx Q. Arguilla et al., "Synthesis and Stability of Two-Dimensional Ge/Sn Graphane Alloys", Chemistry of materials, vol. 26, Nov. 12, 2014, pp. 6941-6946.

Fan Fan, "Exfoliation and Stability Studies of Germanane and its Derivatives", Undergraduate Research Thesis, The Ohio State University, Nov. 2014.

* cited by examiner

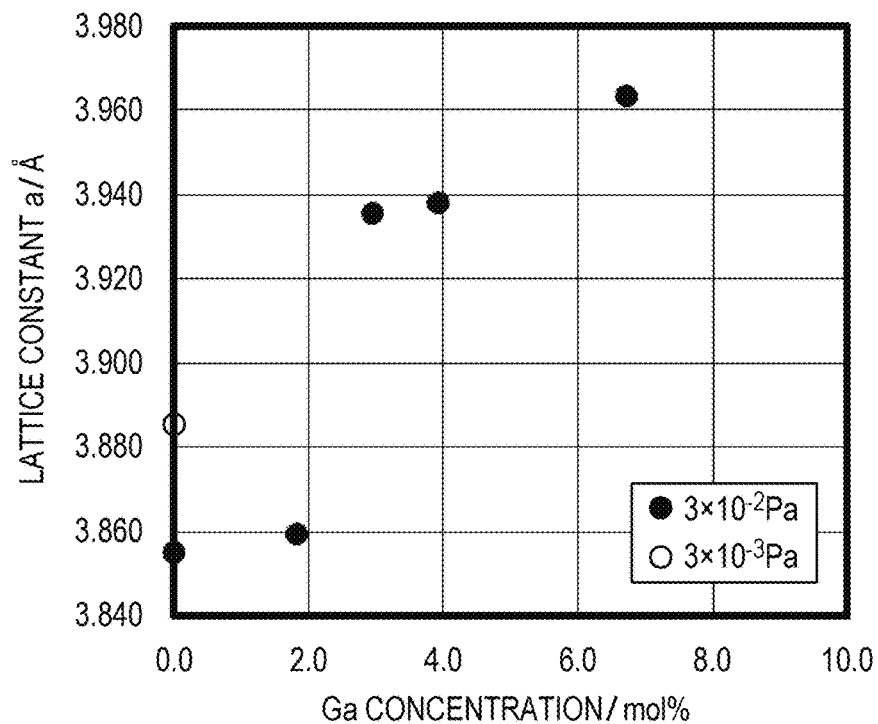
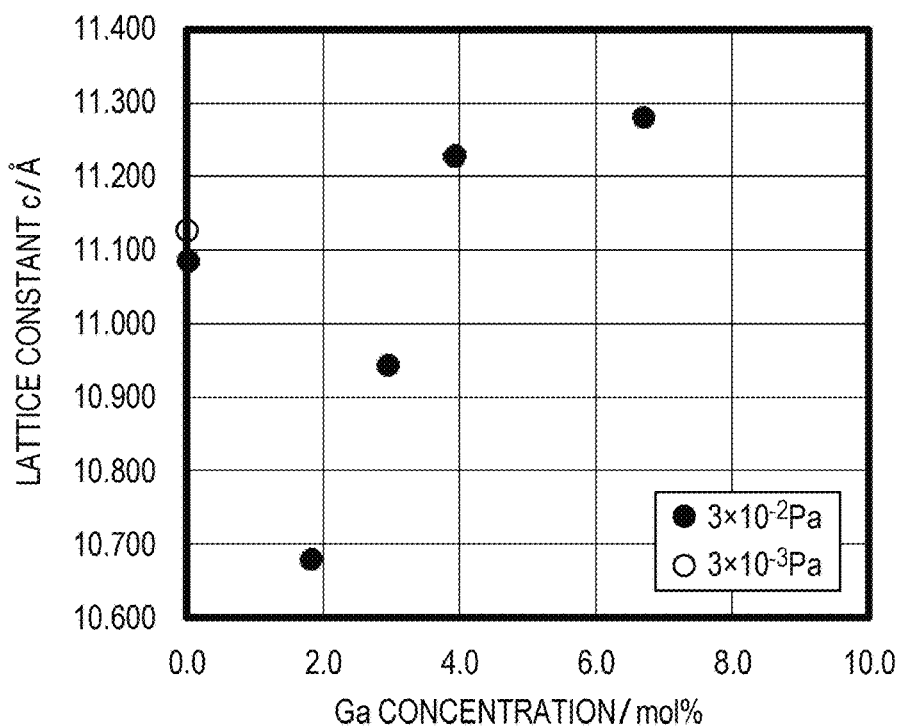

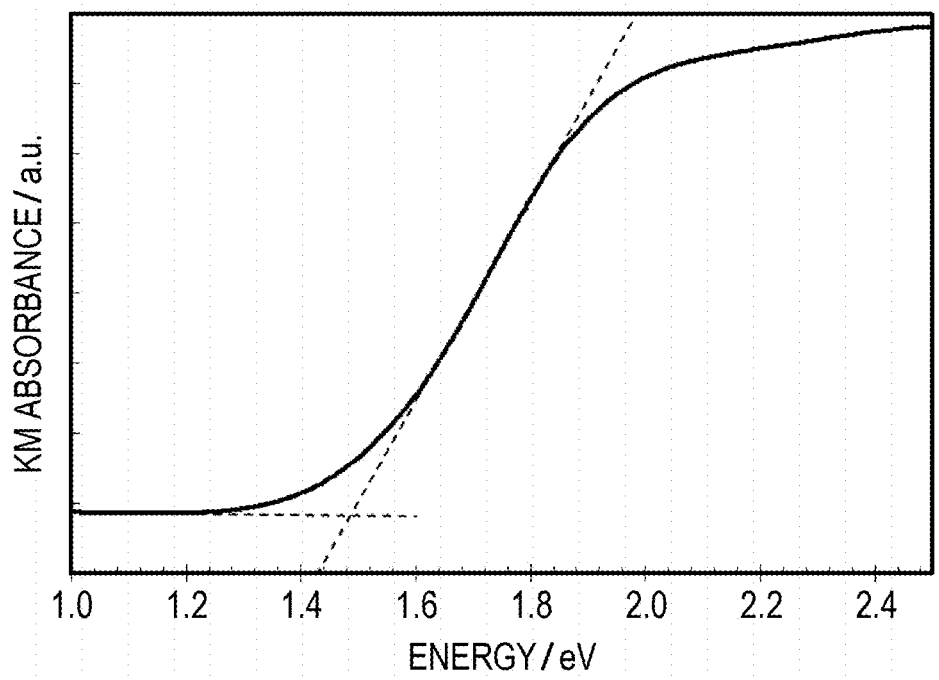

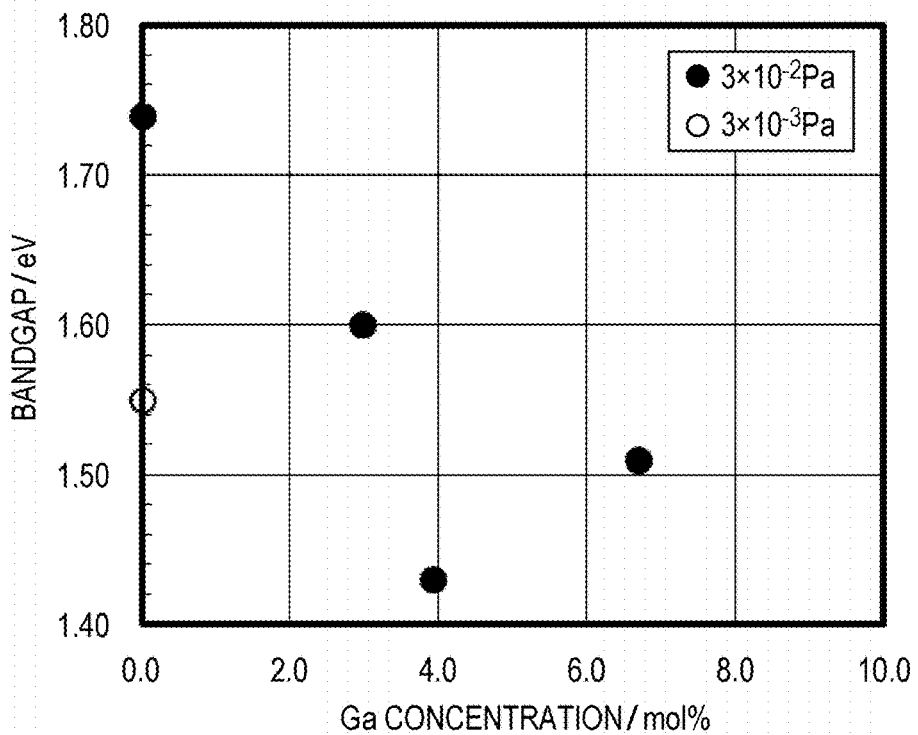
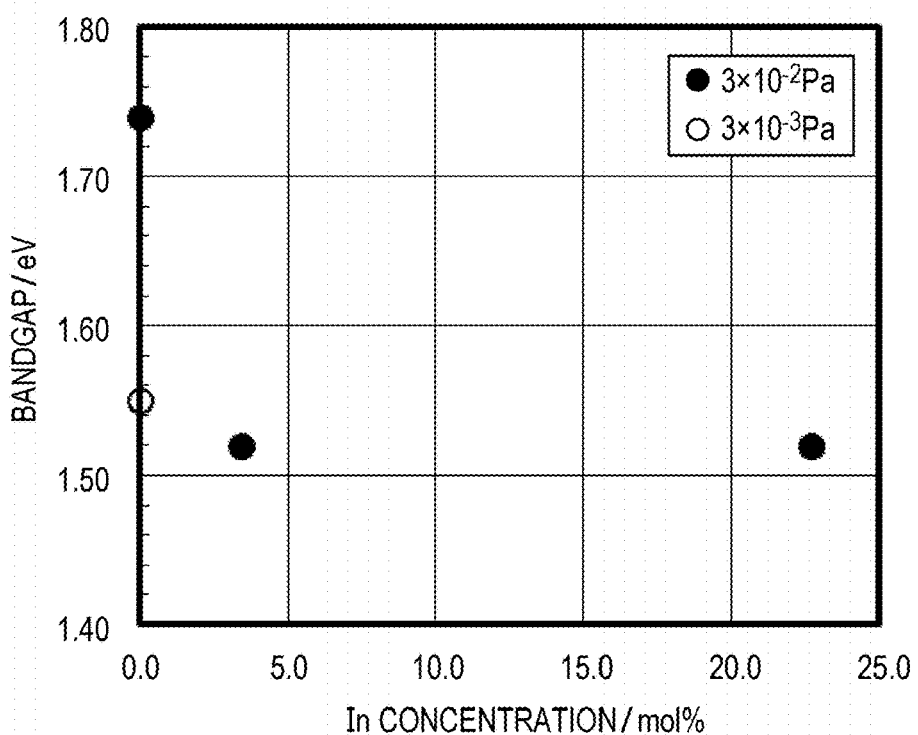

PHOTOELECTRIC CONVERSION MATERIAL AND SOLAR CELL USING THE SAME

BACKGROUND

1. Technical Field

The present disclosure relates to a photoelectric conversion material and particularly to a light-absorbing or charge separation material for solar cells. The present disclosure also relates to a solar cell using the photoelectric conversion material.

2. Description of the Related Art

Graphene is a layered compound having $SP^2$ hybridization, and silicene and germanene are layered compounds having mixed $SP^2$-$SP^3$ hybridization. These layered compounds have high mobility and are semimetals with no bandgap. By hydrogenating graphene, silicene, and germanene, graphane (CH), silicane (SiH), and germanane (GeH), respectively, having $SP^3$ hybridization are obtained. These compounds have a bandgap. Among them, graphane has the largest bandgap, and germanane has the smallest bandgap.

FIG. 13A is an illustration showing the crystal structure of germanane as viewed in the direction of its C axis, and FIG. 13B is an illustration showing the crystal structure of germanane as viewed in a direction perpendicular to the C axis.

Elisabeth Bianco et al., ACS Nano, March 2013, Vol. 7, No. 5, pp. 4414-4421 report that the bandgap of germanane is 1.59 eV. It is also stated that the electron mobility in germanane is estimated to be 18,195 $cm^2$/(Vs).

Maxx Q. Arguilla et al., Chemistry of materials, November 2014, Vol. 26, pp. 6941-6946 and Fan Fan, Exfoliation and Stability Studies of Germanane and its Derivatives, Undergraduate Research Thesis, The Ohio State University, November 2014 disclose germanane derivatives obtained by partial replacement of germanium with other elements.

SUMMARY

There is a need for further improvement in the performance of solar cells.

One non-limiting and exemplary embodiment provides a photoelectric conversion material including a germanane derivative and capable of improving the performance of a solar cell.

In one general aspect, the techniques disclosed here feature a photoelectric conversion material comprising a germanane derivative having a composition represented by $Ge_XM_YH_Z$, wherein M includes at least one of Ga and In, and $X \geq Y$, $X \geq Z > 0$, and $X+Y=1$ are satisfied.

It should be noted that general or specific embodiments may be implemented as an element, a device, a module, a system, an integrated circuit, a method, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 6A is a graph showing the Ga doping concentration dependence of the lattice constant "a" of a germanane derivative;

FIG. 6B is a graph showing the Ga doping concentration dependence of the lattice constant "c" of the germanane derivative;

FIG. 8C is a graph showing the DRA spectrum of the compound $(Ge_{0.933}Ga_{0.067}H_{0.933})$ in Example 4;

FIG. 11A is a graph showing the Ga doping concentration dependence of the bandgap of a germanane derivative;

FIG. 11B is a graph showing the In doping concentration dependence of the bandgap of a germanane derivative;

DETAILED DESCRIPTION

Figure 1A:
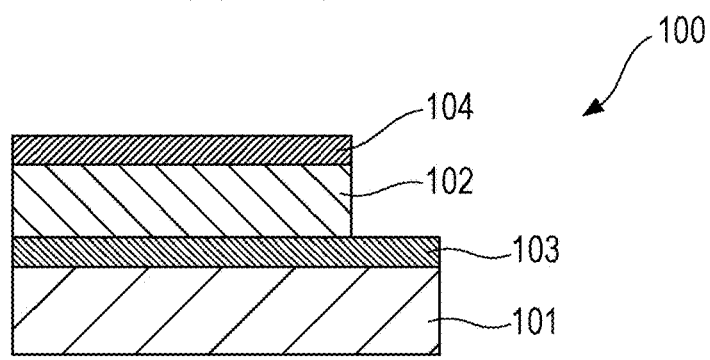
FIG. 1A is a cross-sectional view schematically showing an example of a solar cell.

Underlying knowledge forming the basis of the present disclosure is as follows.

As described above, germanane and its derivatives have high electron mobility. The mobility μ of carriers (electrons in this case) is one of the factors determining the diffusion length of the carriers. As can be seen from the following formulas, as the mobility μ increases, the diffusion length L of the carriers increases.

$$L = \sqrt{D \cdot \tau_{bulk}}$$

$$D = \frac{kT}{q}\mu$$

$$\mu = \frac{q\tau_s}{m^*}$$

D: diffusion constant, $\tau_{bulk}$: carrier lifetime, k: Boltzmann constant, T: absolute temperature, q: electric charge, $m^*$: effective mass, $\tau_s$: relaxation time When high-mobility germanane or its derivative is used as a photoelectric conversion material of a solar cell, the diffusion length L of carriers generated by light absorption is large, and therefore the carriers can easily reach an electrode without electron-hole recombination. Since the amount of current that can be outputted to the outside increases, the performance of the solar cell is expected to be improved.

It is known that the performance of a photoelectric conversion material for solar cells depends on its bandgap. The details are described in William Shockley et al., Journal of Applied Physics, March 1961, Vol. 32, No. 3, pp. 510-519. The limit of conversion efficiency is known as the Shockley-Queisser limit. When the bandgap is 1.4 eV, the theoretical conversion efficiency is maximum. When the bandgap is larger than 1.4 eV, a high open-circuit voltage is obtained, but the value of short-circuit current decreases because the absorption wavelength decreases. When the bandgap is less than 1.4 eV, the value of short-circuit current increases because the absorption wavelength increases, but the open-circuit voltage decreases.

As described above, the bandgap of germanane is 1.59 eV, which is larger than 1.4 eV that gives the maximum theoretical efficiency. There is therefore a need for a germanane derivative having a bandgap closer to 1.4 eV. When such a germanane derivative is used as a light-absorbing material for a solar cell, the solar cell obtained can have higher conversion efficiency than conventional solar cells.

The present inventors have found that, by doping germanane with gallium (Ga) or indium (In), which is a group 13 element, to partially replace Ge with Ga or In, the bandgap can be reduced while a reduction in electron mobility is prevented.

By adjusting the bandgap to a value closer to 1.4 eV, a photoelectric conversion material that can provide higher conversion efficiency when used for a solar cell can be obtained. Germanane has $SP^3$ hybridization. However, by partially replacing Ge with Ga or In, part of the $SP^3$ hybridization become $SP^2$ hybridization, and the in-plane motion of electrons is facilitated. Therefore, even when Ge is partially replaced with Ga or In, the high electron mobility can be maintained. The high electron mobility and the desired bandgap can thereby be achieved simultaneously.

An outline of an aspect of the present disclosure is as follows.

A photoelectric conversion material in the aspect of the present disclosure comprises a germanane derivative having a composition represented by $Ge_XM_YH_Z$, wherein M includes at least one of Ga and In, and $X \geq Y$, $X \geq Z > 0$, and $X+Y=1$ are satisfied.

The germanane derivative may have a crystal structure belonging to, for example, space group $P6_3mc$.

For example, Y may be 0.005 or more and 0.227 or less.

For example, M may be Ga, and Y may be 0.005 or more and 0.067 or less.

For example, Y may be 0.039 or more and 0.067 or less.

For example, M may be In, and Y may be 0.005 or more and 0.227 or less.

For example, Y may be 0.034 or more and 0.227 or less.

For example, a bandgap of the germanane derivative may be 1.22 eV or more and 1.58 eV or less.

For example, a bandgap of the germanane derivative may be 1.43 eV or more and 1.58 eV or less.

A solar cell in an aspect of the present disclosure comprises: a first electrode having electrical conductivity; a second electrode having electrical conductivity; and a light-absorbing layer between the first electrode and the second electrode, the light-absorbing layer converting incident light into electric charge, wherein the light-absorbing layer includes the photoelectric conversion material described above.

Embodiments

A photoelectric conversion material in an embodiment includes a germanane derivative in which Ge in germanane is partially replaced with at least one of Ga and In.

The germanane derivative in the present embodiment has a composition represented by $Ge_XM_YH_Z$ (0<X, 0<Y, and 0<Z). M includes at least one of Ga and In. The molar ratio X of Ge (hereinafter referred to as the Ge ratio), the molar ratio Y of M (hereinafter referred to as the M ratio), and the molar ratio Z of H (hereinafter referred to as the H ratio) satisfy relations represented by the following formulas (1) to (3).

$$X+Y=1 \tag{1}$$

$$X \geq Y \tag{2}$$

$$X \geq Z \tag{3}$$

The following formula (4) may be satisfied.

$$0 < Z \leq 1-Y \tag{4}$$

The germanane derivative may have symmetry belonging to space group $P6_3mc$.

The germanane derivative in the present embodiment can be obtained by doping germanane with at least one of Ga and In at a ratio (i.e., a molar ratio Y) of, for example, more than 0 mol % and 30 mol % or less.

The molar ratio Y of M in the germanane derivative may be, for example, 0.005 or more and 0.227 or less. When M is Ga, i.e., when the germanane derivative is $Ge_XGa_YH_Z$, the molar ratio Y may be, for example, 0.005 or more and 0.067 or less, or may be 0.039 or more and 0.067 or less. When M is In, i.e., when the germanane derivative is $Ge_XIn_YH_Z$, the molar ratio Y may be, for example, 0.005 or more and 0.227 or less, or may be 0.034 or more and 0.227 or less. In the above cases, the lower limit of the molar ratio Y is 0.005. However, when the molar ratio Y is larger than 0, a certain effect can be obtained.

In the present embodiment, by partially replacing Ge in GeH with Ga and/or In, the germanane derivative can have a smaller bandgap than germanane while a reduction in electron mobility is prevented, as described above. It is stated in Elisabeth Bianco et al., ACS Nano, March 2013, Vol. 7, No. 5, pp. 4414-4421 that the bandgap of germanane is 1.59 eV, although its production conditions are different. In the present embodiment, by partially replacing Ge in GeH with Ga and/or In, the germanane derivative obtained can have a bandgap smaller than the bandgap of germanane, i.e., smaller than 1.59 eV described in Elisabeth Bianco et al., ACS Nano, March 2013, Vol. 7, No. 5, pp. 4414-4421. The bandgap of the germanane derivative in the present embodiment may be, for example, 1.58 eV or less. The bandgap may be desirably 1.52 eV or less and more desirably 1.50 eV or less. The lower limit of the bandgap may be, for example, 1.22 eV or more and desirably 1.3 eV or more. Within the above range, the bandgap is close to the ideal bandgap of 1.40 eV, and a solar cell having higher conversion efficiency than conventional solar cells can be obtained. The bandgap can be adjusted by changing the doping concentration of Ga or In or the degree of vacuum during annealing.

The germanane derivative in the present embodiment can be synthesized, for example, as follows. First, Ca, Ge, and Ga or In are fired under prescribed conditions to obtain calcium germanide ($CaGe_2$) in which Ge is partially replaced with Ga or In. Next, the obtained calcium germanide in a solid phase state is allowed to react to replace calcium with hydrogen. In this method, germanane (GeH) with Ge partially replaced with Ga or In is synthesized. A specific synthesis method will be described in (Examples).

(Structure of Solar Cell)

The photoelectric conversion material in the present embodiment is desirably applicable to solar cells.

Figure 1B:
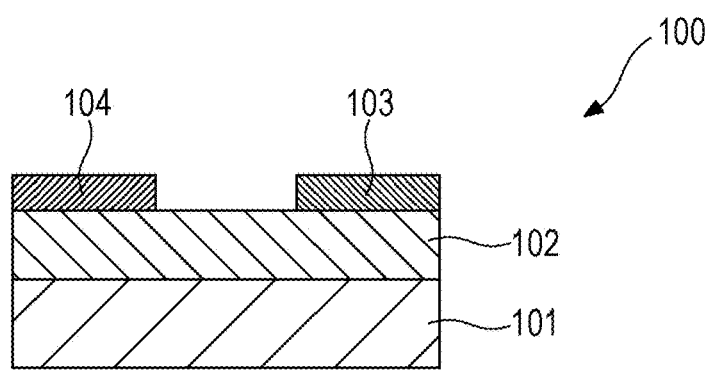
FIG. 1B is a cross-sectional view schematically showing another example of the solar cell.
Figure 1C:
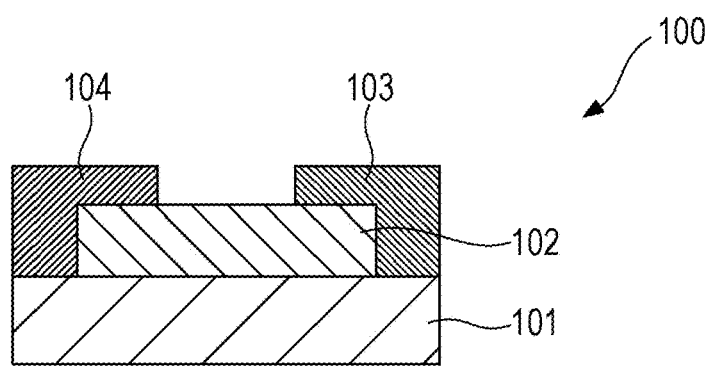
FIG. 1C is a cross-sectional view schematically showing yet another example of the solar cell.

FIGS. 1A to 1C are schematic cross-sectional views showing examples of a solar cell 100 using the photoelectric conversion material in the present embodiment.

In the solar cell 100 in FIG. 1A, a first electrode 103, a light-absorbing layer 102, and a second electrode 104 are stacked in this order on a substrate 101.

In each of the solar cells 100 in FIGS. 1B and 1C, a light-absorbing layer 102 is disposed on a substrate 101, and a first electrode 103 and a second electrode 104 are disposed on the light-absorbing layer 102 with a prescribed space therebetween. In the germanane derivative, the mobility is particularly high in in-plane directions. In the structures shown in FIGS. 1B and 1C, the high mobility in the germanane derivative in the in-plane directions can be effectively utilized.

The light-absorbing layer 102 converts incident light to electric charge. The light-absorbing layer 102 includes the photoelectric conversion material in the present embodiment. The photoelectric conversion material includes the germanane derivative described above. The light-absorbing layer 102 may be obtained by slicing the germanane derivative (a laminar crystal) synthesized by a method described later into a prescribed size. Alternatively, the light-absorbing layer 102 may be formed by growing the germanane derivative on a surface of the substrate or an electrode.

In each solar cell 100, when the light-absorbing layer 102 is irradiated with light from the outside, the light is absorbed, and electrons and holes are generated. The electrons generated in the light-absorbing layer 102 are outputted to the outside through the first electrode 103. The holes generated in the light-absorbing layer 102 are outputted to the outside through the second electrode 104.

The substrate 101 plays a role in physically holding the light-absorbing layer 102, the first electrode 103, and the second electrode 104. For example, a transparent material or a non-transparent material may be used for the substrate 101. Examples of the transparent material include glass and light-transmitting plastics. Examples of the non-transparent material include metals, ceramics, and non-light-transmitting plastics. When a transparent material is used for the substrate 101, the light-absorbing layer 102 may be irradiated with sunlight passing through the substrate 101 to generate electric power.

In the structure in FIG. 1A, when one or both of the first electrode 103 and the second electrode 104 have sufficiently high strength, the substrate 101 may be omitted. The substrate 101 is disposed in contact with the first electrode 103. However, the substrate 101 may be disposed in contact with the second electrode 104.

A conductive material may be used for the first electrode 103 and the second electrode 104. Examples of the conductive material include metals, transparent metal oxide materials, and carbon materials. Examples of the metal material include gold, silver, copper, platinum, aluminum, titanium, nickel, tin, zinc, and chromium. Examples of the transparent metal oxide material include indium-tin complex oxide, antimony-doped tin oxide, fluorine-doped tin oxide, and zinc oxide doped with boron, aluminum, gallium, or indium. Examples of the carbon material include graphene, carbon nanotubes, and graphite.

In particular, in the structure in FIG. 1A, it is desirable that one or both of the first electrode 103 and the second electrode 104 have light transmittance in the ultraviolet to near infrared range. When a non-transparent material is used for one of the first electrode 103 and the second electrode 104, light transparency can be imparted by providing a pattern for light transmission. Examples of the pattern include a grating pattern, a line pattern, and a wavy line pattern.

In the structure in FIG. 1A, when the first electrode 103 and the second electrode 104 have light transparency, it is desirable that the light transmittance of the electrodes 103 and 104 is high. The light transmittance is, for example, 50% or higher and desirably 80% or higher. Desirably, the wavelength range of light transmitting through the electrodes 103 and 104 is wider than the absorption wavelength range of the light-absorbing material included in the light-absorbing layer 102.

Although not illustrated, an electron transport layer may be disposed between the light-absorbing layer 102 and the first electrode 103. By disposing the electron transport layer, the electron extraction efficiency from the first electrode 103 can be improved. The electron transport layer is typically formed from a semiconductor material.

Examples of the semiconductor material used for the electron transport layer include metal oxide materials and organic n-type semiconductor materials. Examples of the metal oxide materials include titanium oxide, tin oxide, zinc oxide, and indium oxide. Examples of the organic n-type semiconductor materials include imide compounds, quinone compounds, fullerenes, and their derivatives.

Although not illustrated, a hole transport layer may be disposed between the light-absorbing layer 102 and the second electrode 104. By disposing the hole transport layer, the hole extraction efficiency from the second electrode 104 can be improved. The hole transport layer is typically formed from a semiconductor material.

Examples of the semiconductor material used for the hole transport layer include inorganic p-type semiconductor materials and organic p-type semiconductor materials. Examples of the inorganic p-type semiconductor materials include CuO, $Cu_2O$, CuSCN, molybdenum oxide, and nickel oxide. Examples of the organic p-type semiconductor materials include phenylamines having a tertiary amine in their structure, triphenylamine derivatives, and PEDOT compounds having a thiophene structure.

Examples

A plurality of germanane derivatives containing different dopants at different concentrations were produced and subjected to analysis. In Examples 1 to 4, germanane derivatives containing Ga were produced. In Examples 5 and 6, germanane derivatives containing In were produced. In Comparative Examples 1 and 2, germanane (GeH) was produced.

Methods for Producing Compounds in Examples and Comparative Examples

Examples 1 to 4

First, a quartz ampule having a closed end was loaded with Ca, Ge, and Ga in a nitrogen atmosphere. The purity of Ca used was 99%, the purity of Ge used was 99.999% or higher, and the purity of Ga used was 99.99%. The materials to be loaded into the quartz ampule were sufficiently mixed in advance in a mortar under a nitrogen atmosphere. The ratio of the number of moles of Ga to ((the number of moles of Ge)+(the number of moles of Ga)) (this ratio is also referred to as the initial prepared ratio) in each Example is shown in Table 1. The ratio of the total number of moles of Ge and Ga used as raw materials of a germanane derivative to the number of moles of Ca was 2.

Next, a rotary pump was used to evacuate the quartz ampule to $3.0 \times 10^{-2}$ Pa, and then an opening of the quartz ampule in the evacuated state was sealed using a burner (oxygen-hydrogen torch).

Next, the mixture was annealed in an electric furnace at 1,000° C. for 18 hours. Then the resulting mixture was cooled to room temperature over three days. In this case, the mixture was cooled to 386° C. in 48 hours in the electric furnace and was then left to cool naturally.

Next, the fired material was immersed in 5 mol/L HCl (aq), i.e., an aqueous HCl solution, for 1 day and washed with ion exchanged water. In this case, a germanane derivative (solid) was separated by spontaneous sedimentation. The separated germanane derivative was further washed with ethanol and dried sufficiently in a vacuum drying oven. Compounds in Examples 1 to 4 were obtained in the method described above.

Examples 5 and 6

Compounds in Examples 5 and 6 were produced using the same method as in Example 1 except that In with a purity of 99.99% was used as a raw material instead of Ga. The molar ratio of In (also referred to as the initial prepared ratio) in each Example is shown in Table 1.

Comparative Examples 1 and 2

Only Ca and Ge were placed in a quartz ampule and fired, washed, and dried using the same method as in Example 1 to thereby produce a compound (GeH) in Comparative Example 1. A compound (GeH) in Comparative Example 2 was produced by the same method as in Comparative Example 1 except that the quartz ampule was evacuated during sintering to $3.0 \times 10^{-3}$ Pa using a turbo-molecular pump.

Figure 2A:
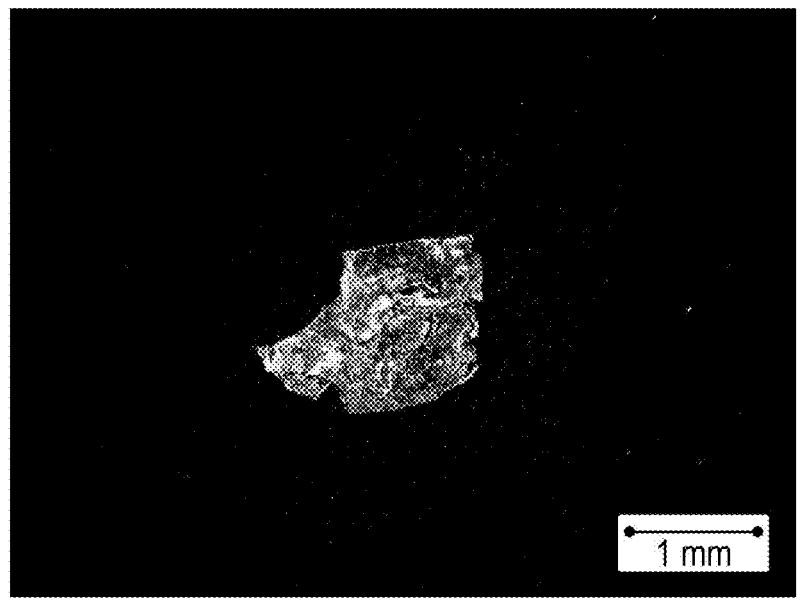
FIG. 2A is a photograph showing a crystal of a compound $(Ge_{0.970}Ga_{0.030}H_{0.970})$ in Example 2.
Figure 2B:
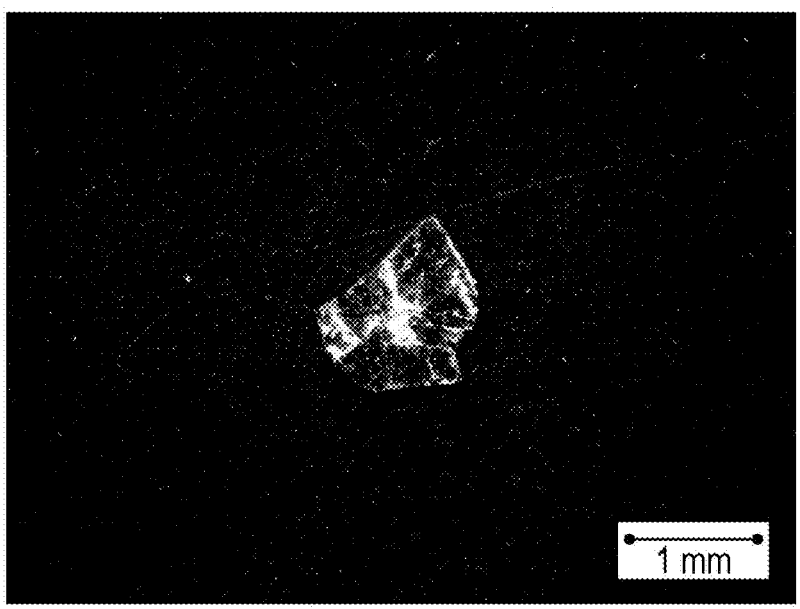
FIG. 2B is a photograph showing a crystal of a compound $(Ge_{0.966}In_{0.034}H_{0.966})$ in Example 5.
Figure 2C:
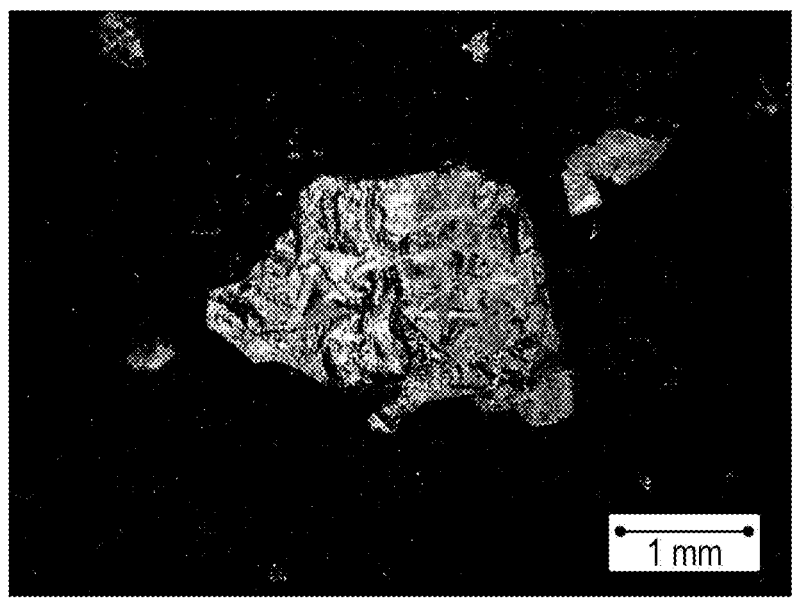
FIG. 2C is a photograph showing a crystal of a compound (GeH) in Comparative Example 1.

Photographs of the compounds in Examples 2 and 5 and Comparative Example 1 are shown in FIGS. 2A, 2B, and 2C, respectively.

<Measurement of Doping Concentration: ICP-AES Measurement>

The doping concentrations of Ga or In in the compounds in Examples 1 to 6 were examined.

First, the compound in each Example was subjected to pretreatment. Specifically, the compound was dissolved in sulfuric acid and nitric acid and diluted with pure water to obtain a solution. For each of the solutions obtained, the doping concentration of Ga or In was measured by ICP-AES (inductively-coupled plasma atomic emission spectrometry). The CIROS-120 manufactured by Spectro was used for the measurement. The measurement results and the composition of each compound are shown in Table 1.

<Lattice Constants: Powder XRD Measurement>

The lattice constants of each of the compounds in the Examples and the Comparative Examples were determined by powder XRD (X-ray diffraction) measurement.

The RINT 2000 manufactured by Rigaku Corporation was used for the XRD measurement, and a vertical goniometer was used as the optical system. The measurement angle range was 10° to 80°, and the scanning speed was 2.3°/m in.

Figure 3:
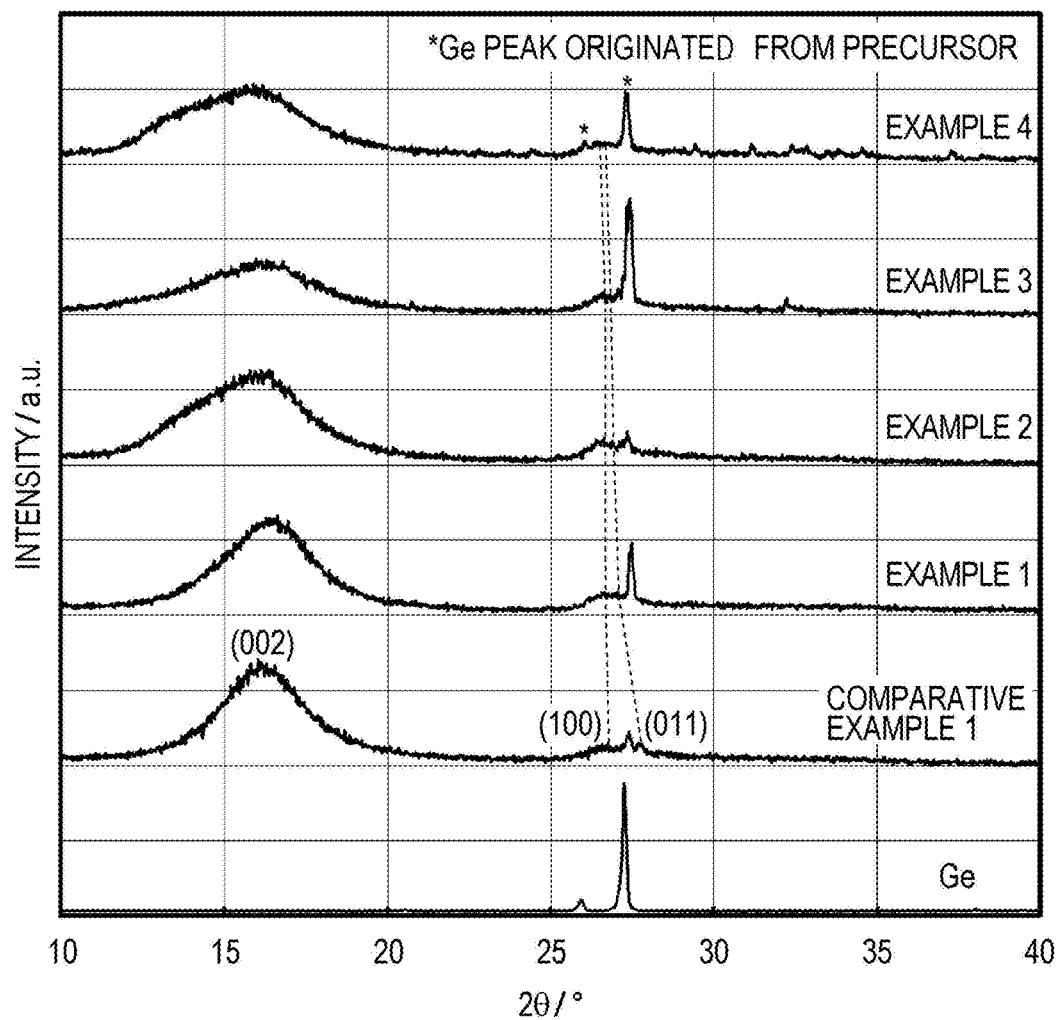
FIG. 3 is a graph showing X-ray diffraction patterns of compounds in Examples 1 to 4 and Comparative Example 1.
Figure 4:
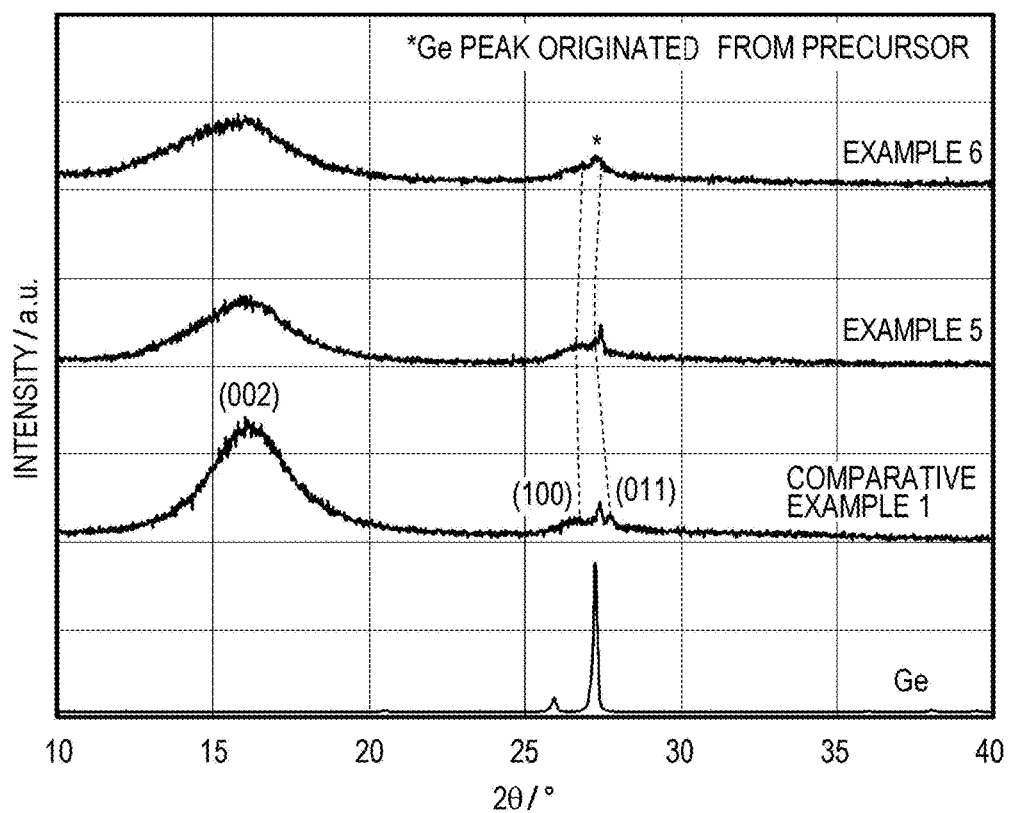
FIG. 4 is a graph showing X-ray diffraction patterns of compounds in Examples 5 and 6 and Comparative Example 1.
Figure 5:
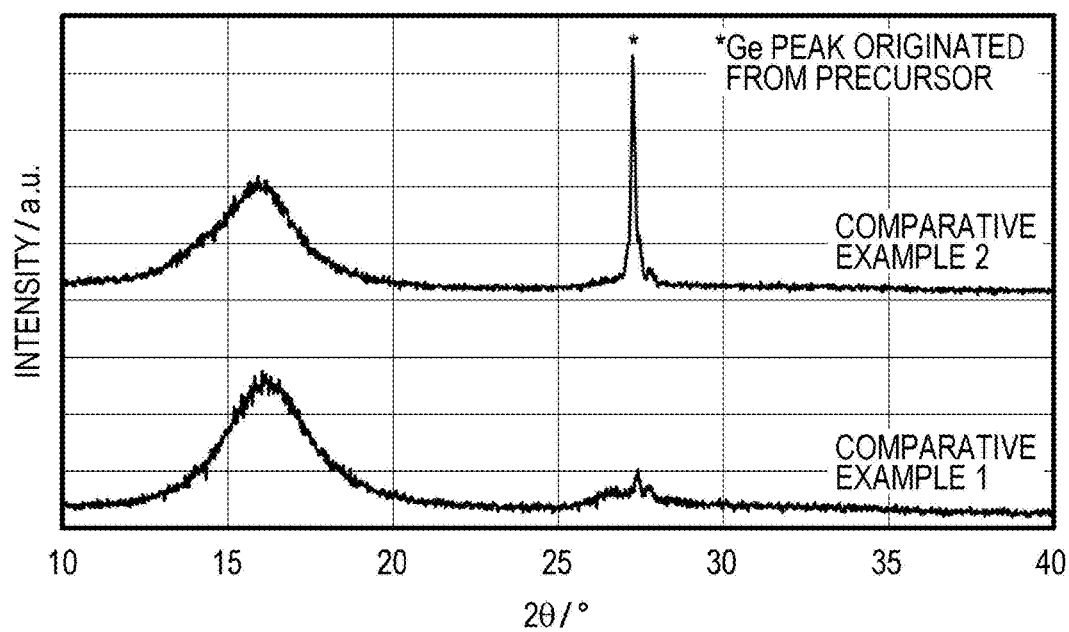
FIG. 5 is a graph showing X-ray diffraction patterns of compounds (GeH) in Comparative Examples 1 and 2.

FIG. 3 is a graph showing the X-ray diffraction patterns of the compounds in Examples 1 to 4 and Comparative Example 1. FIG. 4 is a graph showing the X-ray diffraction patterns of the compounds in Examples 5 and 6 and Comparative Example 1. FIG. 5 is a graph showing the X-ray diffraction patterns of the compounds in Comparative Examples 1 and 2. For comparison, the X-ray diffraction pattern of germanium is also shown in FIGS. 3 and 4. The measurement was performed in the range of 10° to 80°, but the X-ray diffraction patterns in the range of 10° to 40° are shown in FIGS. 3 to 5.

As can be seen from FIGS. 3 to 5, Ge peaks originated from the precursor were found in the range of 25° to 28° in some of the X-ray diffraction patterns in the Examples and the Comparative Examples. The lattice constants of each of the compounds in the Examples and the Comparative Examples were computed using the Cohen method from (002), (100), and (011) peaks on the low-angle side in the measurement results. On the low-angle side, measurement error is considered to be relatively small. The results are shown in Table 1.

Figure 7A:
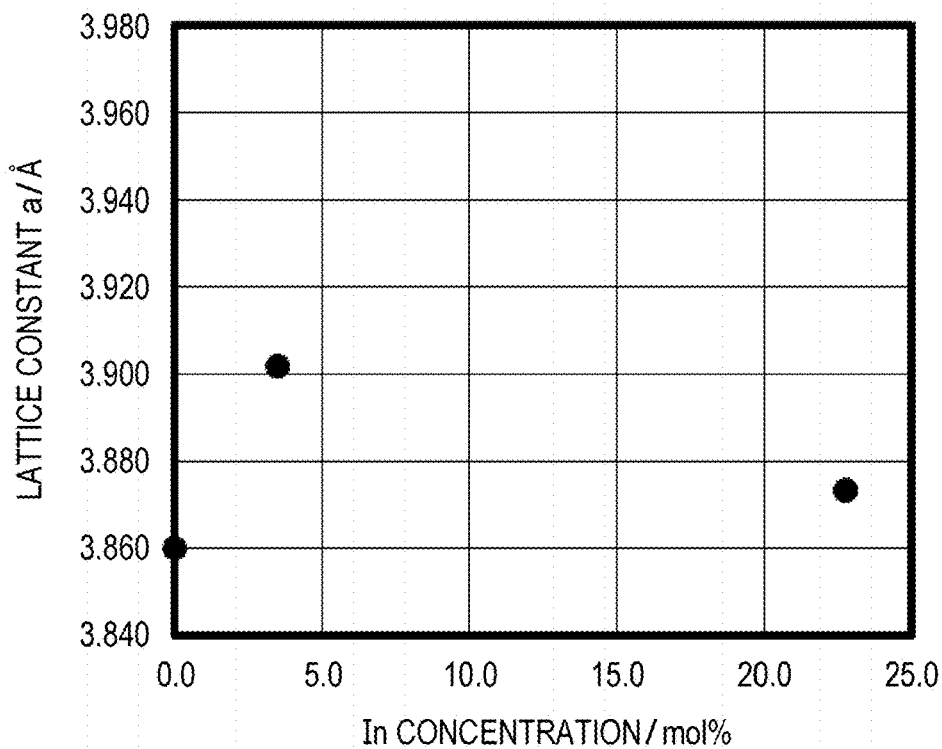
FIG. 7A is a graph showing the In doping concentration dependence of the lattice constant "a" of a germanane derivative.
Figure 7B:
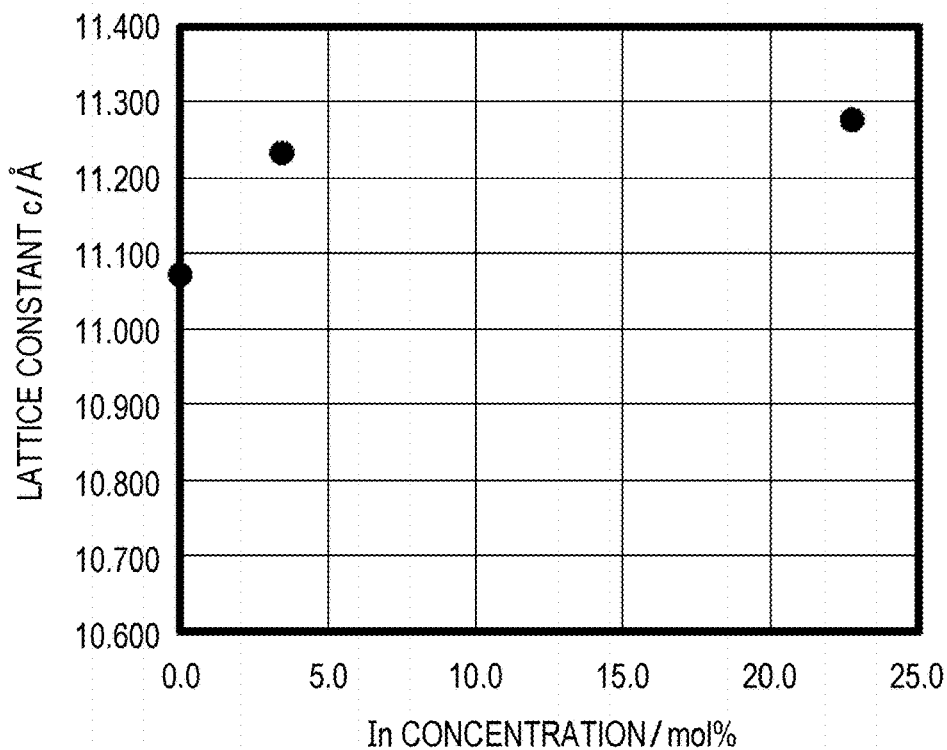
FIG. 7B is a graph showing the In doping concentration dependence of the lattice constant "c" of the germanane derivative.

The relation between the doping concentration of Ga or In and the lattice constants was examined. FIG. 6A is a graph showing the relation between the doping concentration of Ga and the lattice constant "a" in the a-axis direction, and FIG. 6B is a graph showing the relation between the doping concentration of Ga and the lattice constant "c" in the c-axis direction. FIG. 7A is a graph showing the relation between the doping concentration of In and the lattice constant "a" in the a-axis direction, and FIG. 7B is a graph showing the relation between the doping concentration of In and the lattice constant "c" in the c-axis direction.

As can be seen from these results, the doping with Ga or In can increase the lattice constants, and the lattice constants can be larger than those of GeH (Comparative Examples 1 and 2). As can be seen, the lattice constants vary depending on the doping concentration. For example, as the doping concentration of Ga increases, the lattice constant "a" in the a-axis direction and the lattice constant "c" in the c-axis direction increase. In the X-ray diffraction patterns shown in FIGS. 3 and 4, the positions of the peaks of the (002), (100), and (011) planes of the compounds in Examples 1 to 6 correspond to the crystal structure of space group P6₃mc. Therefore, the compounds in Examples 1 to 6 have a crystal structure belonging to space group P6₃mc.

<Bandgap: Diffuse Reflectance Absorption Measurement>

The bandgap of each of the compounds in the Examples and the Comparative Examples was determined by diffuse reflectance absorption measurement.

The UV-3600Plus manufactured by Shimadzu Corporation was used for the diffuse reflectance absorption measurement, and the ISR-603 was used as the integrating sphere. The measurement was performed in a spectral measurement wavelength range of 400 nm to 1,300 nm at a scanning speed of 200 nm/min, using a sampling width of 1.0 nm and a slit width of 32 nm. The incident angle was 0°, and specular reflection was not included. Barium sulfate was used as a standard sample, and a measurement range of 5 mm square was used.

The diffuse reflectance spectrum obtained by the measurement was subjected to Kubelka-Munk transformation to convert it to an absorption spectrum.

Figure 8A:
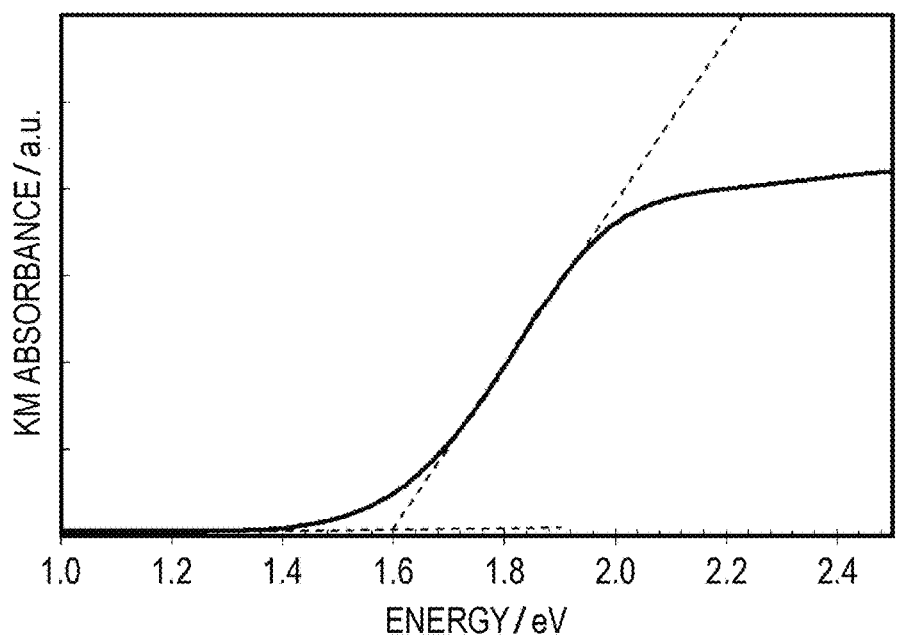
FIG. 8A is a graph showing the DRA spectrum of the compound $(Ge_{0.970}Ga_{0.030}H_{0.970})$ in Example 2.
Figure 8B:
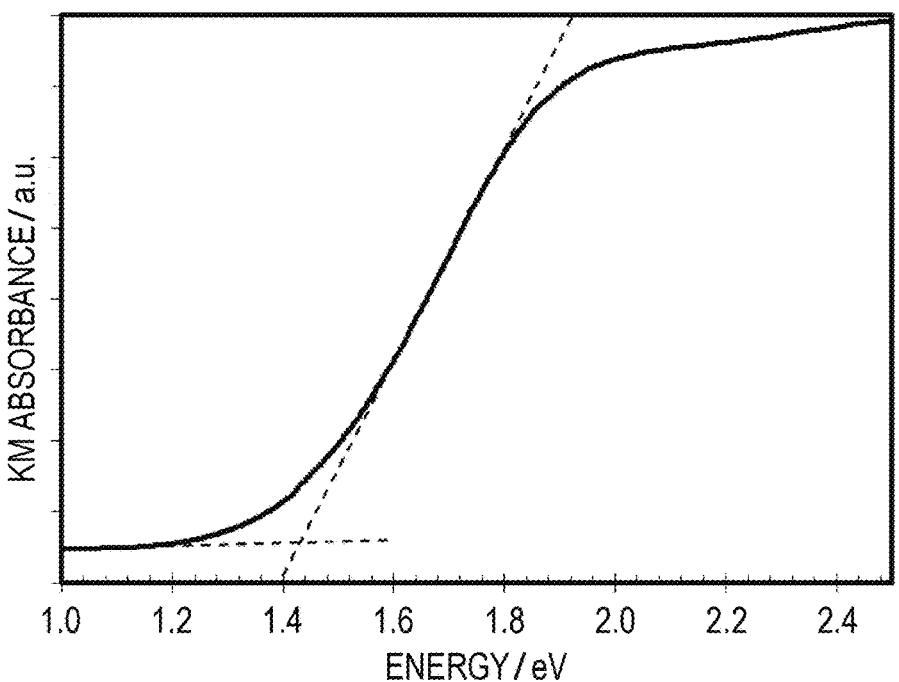
FIG. 8B is a graph showing the DRA spectrum of the compound $(Ge_{0.961}Ga_{0.039}H_{0.961})$ in Example 3.
Figure 9A:
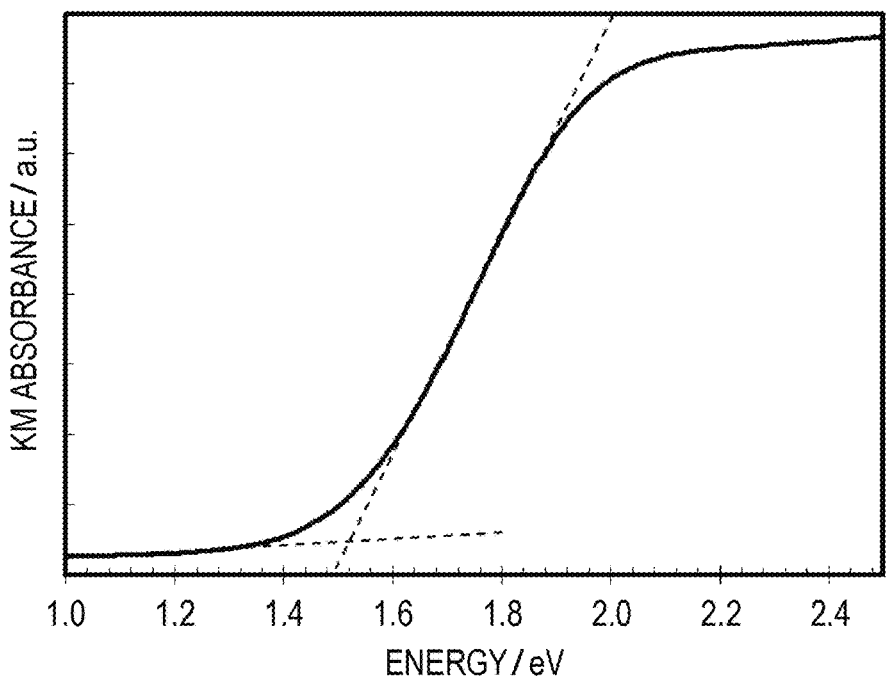
FIG. 9A is a graph showing the DRA spectrum of the compound $(Ge_{0.966}In_{0.034}H_{0.966})$ in Example 5.
Figure 9B:
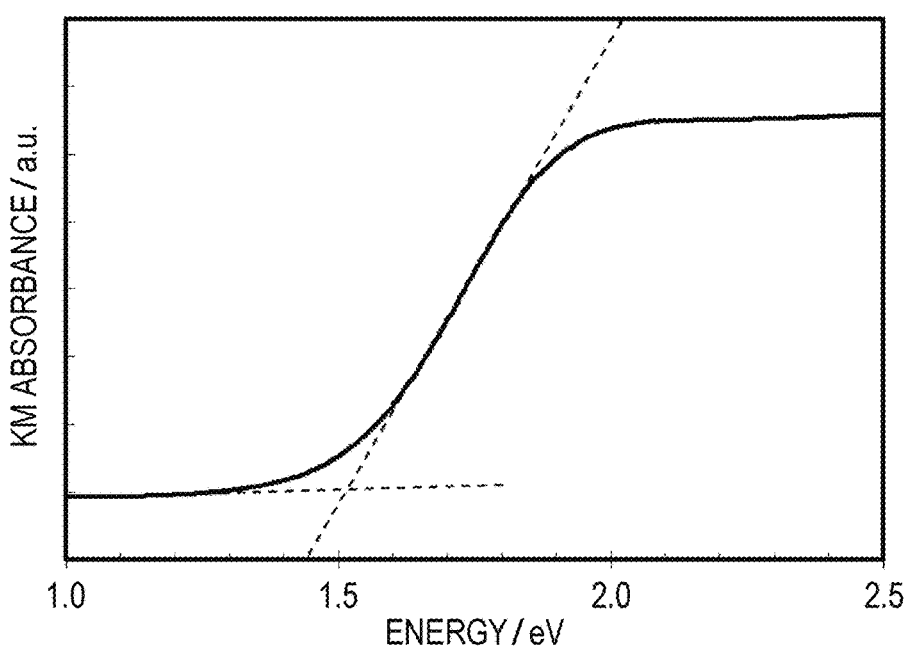
FIG. 9B is a graph showing the DRA spectrum of the compound $(Ge_{0.773}In_{0.227}H_{0.773})$ in Example 6.
Figure 10A:
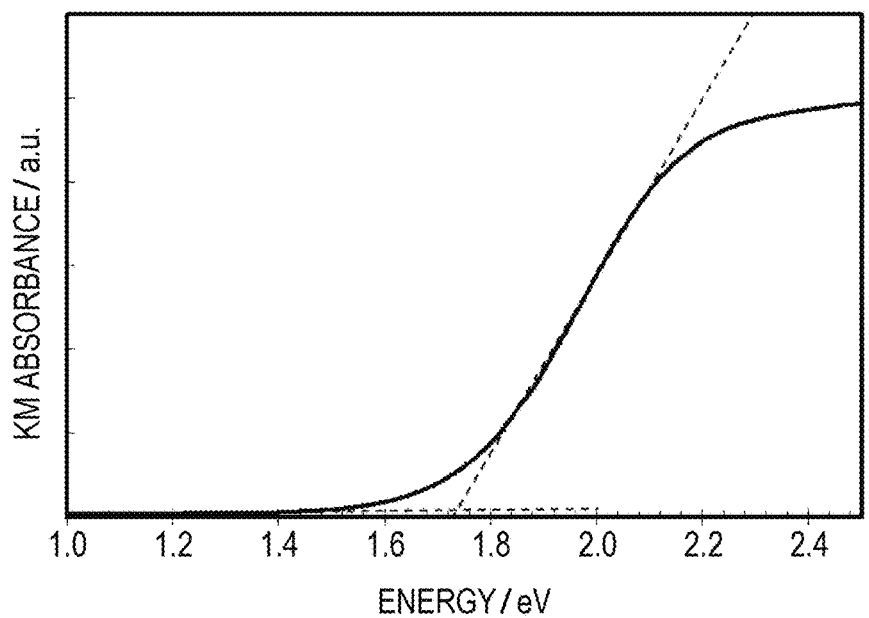
FIG. 10A is a graph showing the DRA spectrum of the compound (GeH) in Comparative Example 1.
Figure 10B:
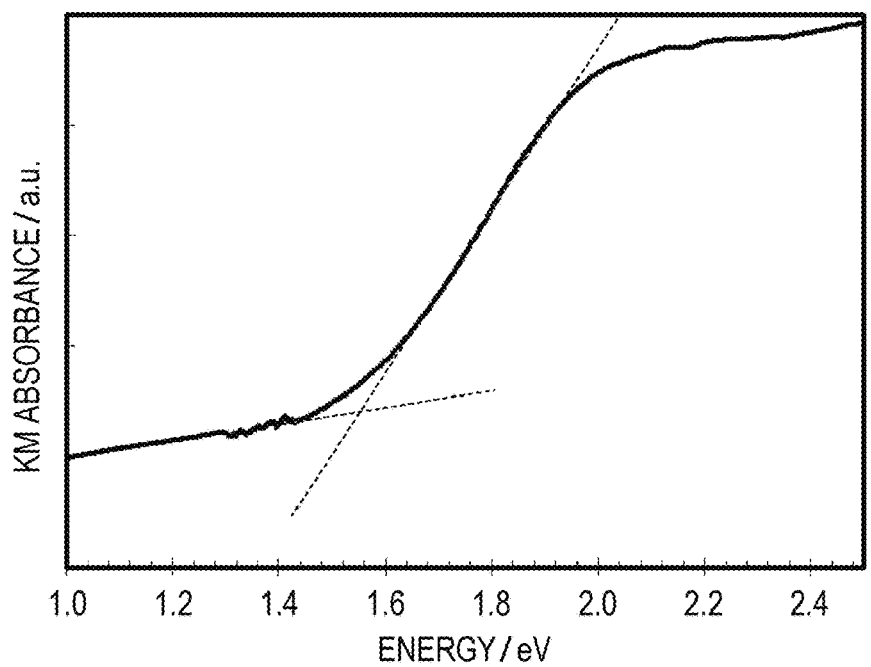
FIG. 10B is a graph showing the DRA spectrum of the compound (GeH) in Comparative Example 2.

FIGS. 8A to 8C are graphs showing the DRA spectra in Examples 2 to 4. FIGS. 9A and 9B are graphs showing the DRA spectra in Examples 5 and 6. FIGS. 10A and 10B are graphs showing the DRA spectra in Comparative Examples 1 and 2.

<FT-IR Measurement>

Next, Fourier transform infrared spectrophotometry (FT-IR) was used to check whether Ge—H bonds were formed in the compounds of Examples 2 and 5 and Comparative Example 1.

The compound in each of Examples 2 and 5 and Comparative Example 1 was subjected to pretreatment. Specifically, the compound was mixed with KBr to produce pellets for analysis. The analyzer used was the iS10 manufactured by Thermo Fisher Scientific, and the detector used was the DLaTGS/KBr. In the measurement, the cumulated number was 128, and the resolution was 4 cm⁻¹.

Figure 12A:
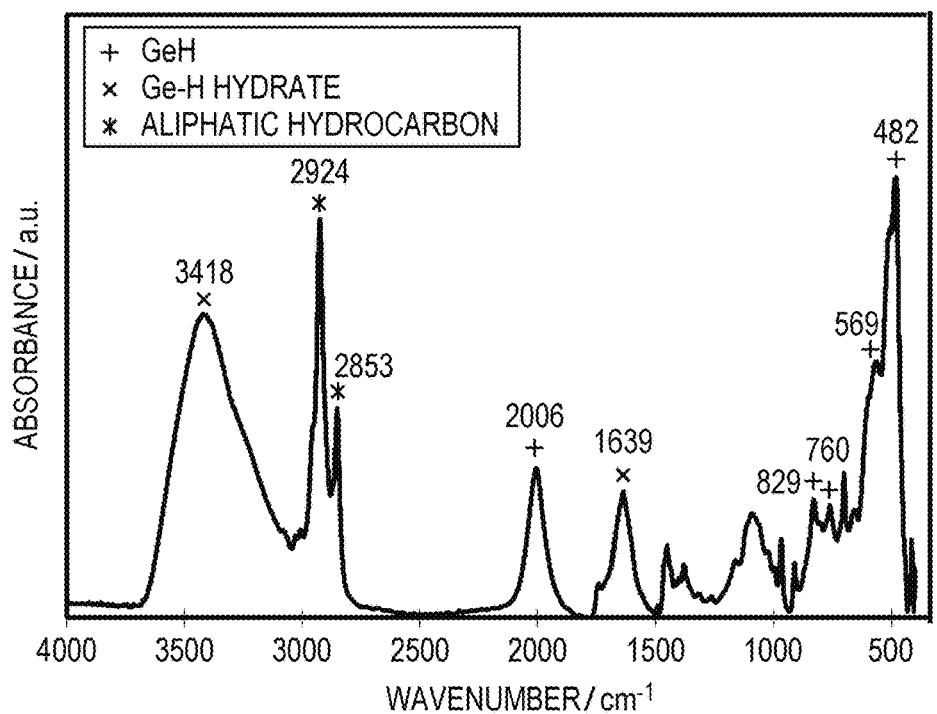
FIG. 12A is a graph showing the FT-IR spectrum of the compound $(Ge_{0.970}Ga_{0.030}H_{0.970})$ in Example 2.
Figure 12B:
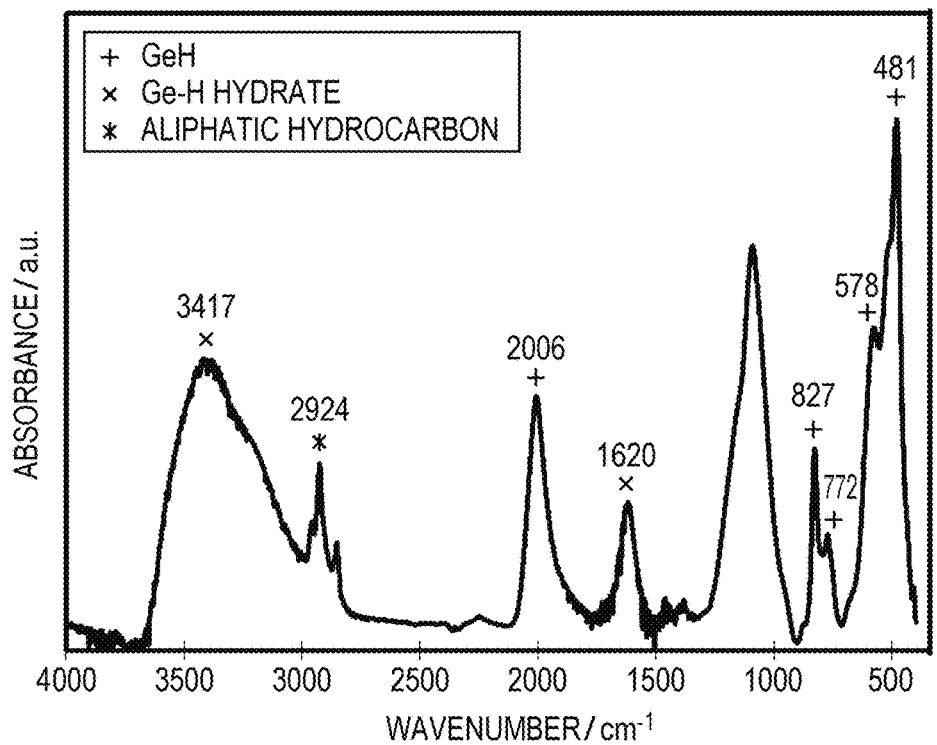
FIG. 12B is a graph showing the FT-IR spectrum of the compound $(Ge_{0.966}In_{0.034}H_{0.966})$ in Example 5.
Figure 12C:
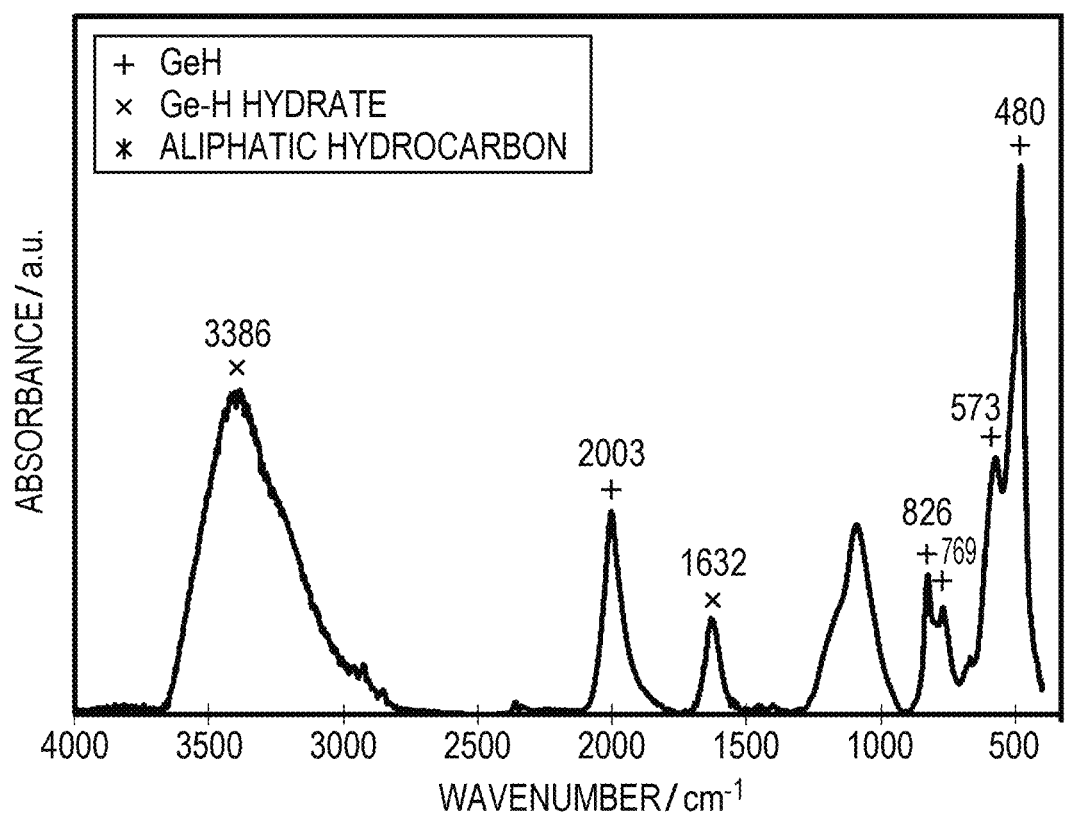
FIG. 12C is a graph showing the FT-IR spectrum of the compound (GeH) in Comparative Example 1.
Figure 13A:
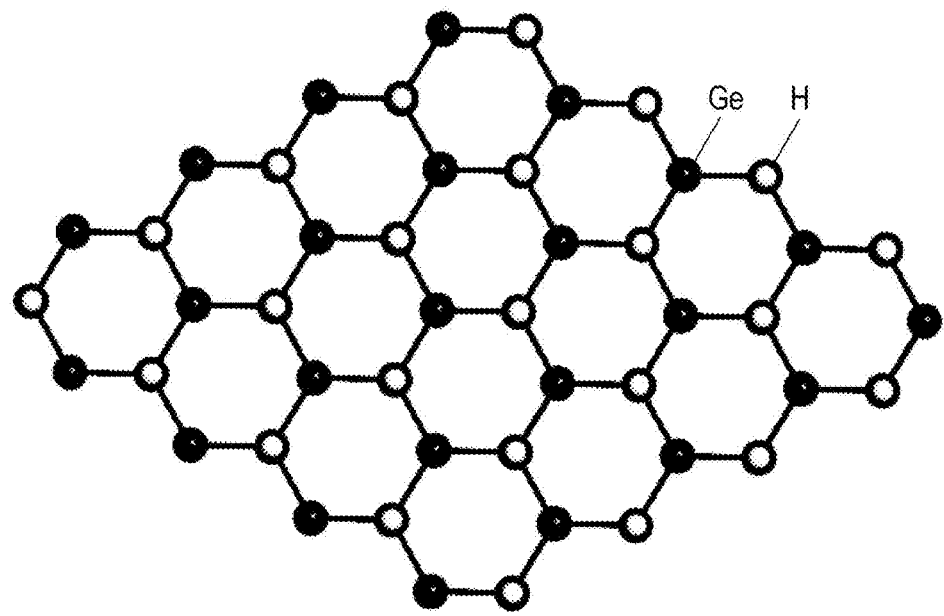
FIG. 13A is a plan view showing the crystal structure of germanane as viewed in the direction of its c axis.
Figure 13B:
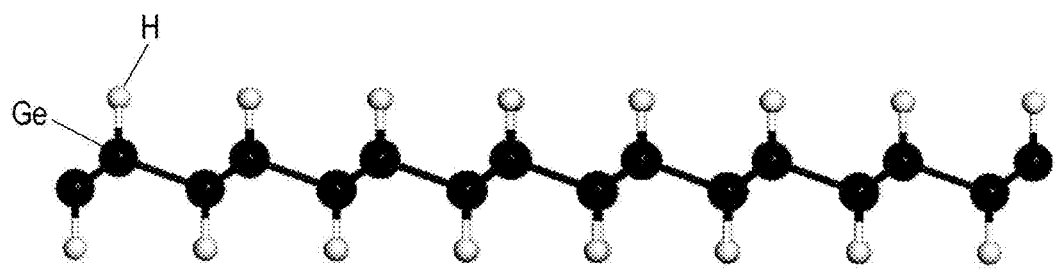
FIG. 13B is a cross-sectional view of the crystal structure of germanane.

FIGS. 12A to 12C are graphs showing the absorption spectra of the compounds in Examples 2 and 5 and Comparative Example 1.

As can be seen from the analysis results, a Ge—H stretching mode peak was detected at 2006 cm$^{-1}$ to 2003 cm$^{-1}$, and Ge—H wagging mode peaks were detected at 829 cm$^{-1}$ to 826 cm$^{-1}$, 772 cm$^{-1}$ to 760 cm$^{-1}$, 578 cm$^{-1}$ to 569 cm$^{-1}$, and 482 cm$^{-1}$ to 480 cm$^{-1}$. The peaks of a Ge—H hydrate or Ge—H hydrates were detected at 3,418 cm$^{-1}$ to 3,386 cm$^{-1}$ and 1,639 cm$^{-1}$ to 1,620 cm$^{-1}$. The peaks of an aliphatic hydrocarbon, which is an impurity mixed during the material synthesis process, were detected at 2,924 cm$^{-1}$ and 2,853 cm$^{-1}$. The formation of Ge—H bonds was observed also in the Ga or In doped compounds in Examples 2 and 5.

TABLE 1

|  | Initial prepared ratio of In or Ge (mol %) | Doping concentration of Ga or In (mol %) | Composition | Lattice constant | | Bandgap (eV) |
| --- | --- | --- | --- | --- | --- | --- |
|  |  |  |  | a (Å) | c (Å) |  |
| Example 1 | Ga: 2.16 | Ga: 1.82 | $Ge_{0.982}Ga_{0.018}H_{0.982}$ | 3.860 | 10.681 | — |
| Example 2 | Ga: 3.75 | Ga: 2.95 | $Ge_{0.970}Ga_{0.030}H_{0.970}$ | 3.936 | 10.944 | 1.60 |
| Example 3 | Ga: 5.97 | Ga: 3.92 | $Ge_{0.961}Ga_{0.039}H_{0.961}$ | 3.938 | 11.229 | 1.43 |
| Example 4 | Ga: 10.03 | Ga: 6.70 | $Ge_{0.933}Ga_{0.067}H_{0.933}$ | 3.964 | 11.282 | 1.51 |
| Example 5 | In: 3.00 | In: 3.44 | $Ge_{0.966}Ga_{0.034}H_{0.966}$ | 3.902 | 11.235 | 1.52 |
| Example 6 | In: 9.87 | In: 22.7 | $Ge_{0.773}Ga_{0.227}H_{0.773}$ | 3.873 | 11.279 | 1.52 |
| Comparative Example 1 | — | — | GeH | 3.860 | 11.074 | 1.74 |
| Comparative Example 2 | — | — | GeH | 3.886 | 11.127 | 1.55 |

Next, the bandgaps in the Examples and the Comparative Examples were computed from the absorption spectra obtained. The results are shown in Table 1.

The relation between the doping concentration of Ga or In and the bandgap was examined. FIG. 11A shows the relation between the doping concentration of Ga and the bandgap of the germanane derivative, and FIG. 11B shows the relation between the doping concentration of In and the bandgap of the germanane derivative.

As can be seen from these results, the doping with Ga or In can reduce the bandgap, and the bandgap can be lower than that of germanane (Comparative Example 1), irrespective of the doping concentration. Although not illustrated, the effect of reducing the bandgap may be obtained even when the doping amount of Ga or In is very small (e.g., about 0.005). In particular, when the doping concentration of Ga is 0.039 or more and 0.067 or less, the bandgap can be further reduced and can be closer to 1.40 eV.

As can be seen from the results in Comparative Examples 1 and 2, the bandgap tends to decrease as the degree of vacuum increases during sintering. Therefore, by doping with Ga or In and increasing the degree of vacuum during sintering, a lower bandgap may be obtained.

The composition of the germanane derivative in the present embodiment is not limited to the compositions in Examples 1 to 6. Although not shown in the Examples, $Ge_XGa_{Y1}In_{Y2}H_Z$ (X+Y1+Y2=1) may be synthesized by doping with both Ge and In. Also in this case, the effects in the above Examples are obtained. In Table 1, the compositions of the compounds in Examples 1 to 6 are based on the assumption that Ge is fully hydrogenated. However, Ge is not necessarily fully hydrogenated. Since the influence of the hydrogenation ratio of Ge is small, the same effects are obtained. Specifically, in $Ge_X(Ga \text{ or } In)_YH_Z$, the relation X≥Z>0 may hold.

The photoelectric conversion material of the present disclosure is useful as a material for a light-absorbing layer of a solar cell. The photoelectric conversion material is applicable to devices for conversion of light to electricity such as optical sensors and light-emitting devices.

What is claimed is:

1. A photoelectric conversion material comprising a germanane derivative having a composition represented by $Ge_XM_YH_Z$, wherein
M includes at least one of Ga and In, and
X≥Y, X≥Z>0, and X+Y=1 are satisfied.

2. The photoelectric conversion material according to claim 1, wherein the germanane derivative has a crystal structure belonging to space group P6$_3$mc.

3. The photoelectric conversion material according to claim 1, wherein Y is 0.005 or more and 0.227 or less.

4. The photoelectric conversion material according to claim 3, wherein
M is Ga, and
Y is 0.005 or more and 0.067 or less.

5. The photoelectric conversion material according to claim 4, wherein Y is 0.039 or more and 0.067 or less.

6. The photoelectric conversion material according to claim 3, wherein
M is In, and
Y is 0.005 or more and 0.227 or less.

7. The photoelectric conversion material according to claim 6, wherein Y is 0.034 or more and 0.227 or less.

8. The photoelectric conversion material according to claim 1, wherein a bandgap of the germanane derivative is 1.22 eV or more and 1.58 eV or less.

9. The photoelectric conversion material according to claim 8, wherein the bandgap of the germanane derivative is 1.43 eV or more and 1.58 eV or less.

10. A solar cell comprising:
a first electrode having electrical conductivity;
a second electrode having electrical conductivity; and
a light-absorbing layer between the first electrode and the second electrode, the light-absorbing layer converting incident light into electric charge, wherein
the light-absorbing layer includes the photoelectric conversion material according to claim 1.

* * * * *